United States Patent [19]

Stein et al.

[11] Patent Number: 5,399,563
[45] Date of Patent: Mar. 21, 1995

[54] BENZYLIDENEQUINUCLIDINONES

[75] Inventors: Ingeborg Stein, Erzhausen; Roland Martin, Weinheim; Michael Casutt, Heppenheim; Ulrich Heywang; Henning Bottcher, both of Darmstadt; Gunther Holzemann, Seeheim, all of Germany

[73] Assignee: Merck Patent Gesellschaft mit beschrankter Haftung, Darmstadt, Germany

[21] Appl. No.: 84,496

[22] Filed: Jul. 1, 1993

[30] Foreign Application Priority Data

Jul. 2, 1992 [DE] Germany ............... 42 21 740.7

[51] Int. Cl.⁶ ............................................. A61K 7/44
[52] U.S. Cl. ................................. 514/305; 546/137
[58] Field of Search ..................... 546/137; 514/305

[56] References Cited

U.S. PATENT DOCUMENTS

| | | | |
|---|---|---|---|
| 4,952,392 | 8/1990 | Thame | 424/58 |
| 5,000,961 | 3/1991 | Lang et al. | 424/451 |
| 5,178,852 | 1/1993 | Forestier et al. | 424/60 |

OTHER PUBLICATIONS

*Chem. Abstracts*, vol. 108, 1988, abstract No. 68304f.
*Chem. Abstracts*, vol. 106, 1987, abstract No. 43843b.
*Chem. Abstracts*, vol. 105, 1986, abstract No. 78870q.

Warawa et al., *Journal of Organic Chemistry*, Bd. 39, Nr. 24, 1974 pp. 3511–3516.

*Primary Examiner*—Johann Richter
*Assistant Examiner*—Catherine S. Kilby Scalzo
*Attorney, Agent, or Firm*—Millen, White, Zelano & Branigan

[57] ABSTRACT

The invention relates to benzylidene-quinuclidinone derivatives of the formula I

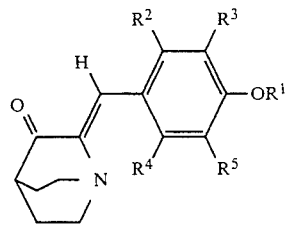

in which
$R^1$ is A;
$R^2$, $R^3$, $R^4$ and $R^5$ are in each case independently of one another H, A, OA or OH; and
A is a straight-chain or branched alkyl radical having 1 to 10 C atoms and processes for their preparation and their use in cosmetic and/or pharmaceutical preparations.

13 Claims, No Drawings

BENZYLIDENEQUINUCLIDINONES

SUMMARY OF THE INVENTION

The invention relates to Benzylidenequinuclidinone compounds of the formula I $$\text{Formula I}$$

in which
$R^1$ is A,
$R^2$, $R^3$
$R^4$ and $R^5$ are in each case independently of one another H, A, OA or OH
and
A is a straight-chain or branched alkyl radical having 1 to 10 C atoms
their salts and processes for their preparation, and their use in cosmetic and/or pharmaceutical preparations, in particular for protection from solar irradiation, or UV rays, and for the prevention and/or treatment of inflammations and allergies of the skin or certain types of cancer.

As is known, the skin is sensitive to solar rays, which can cause a normal sunburn or an erythema, but also more or less pronounced burns.

However, solar rays also have other negative effects: for example they cause the skin to lose its elasticity and form wrinkles and thus lead to premature ageing. Dermatoses can sometimes also be observed. In extreme cases, skin cancer may occur.

It is known that the components present in cosmetic preparations are not always sufficiently stable to light and decompose under the action of light rays and thus lose their effect.

As is known, the most dangerous part of the solar rays is formed by the ultraviolet rays having a wavelength of less than 400 nm. It is also known that owing to the presence of the ozone layer of the earth's atmosphere, which absorbs a part of the solar radiation, the lower limit of the ultraviolet rays which reach the earth's surface is about 280 nm.

It thus appears desirable to make compounds available which can absorb UV rays in a wavelength range from 280 to 400 nm.

UV-B rays having a wavelength between 280 and 320 nm have a special role, in particular in the formation of sun erythemas. UV-A rays having a wavelength between 320 nm and 400 nm in particular ensure the bronzing of the skin, but also its aging They also favor the induction of erythematous skin reactions and in some cases produce phototoxic or photoallergic changes in the skin.

The sun protection filters customary today in the field of cosmetics are divided into UVA or UVB filters. While in the UVB range (280–320 nm) good filters are provided by substances such as Eusolex® 6300 or Eusolex® 232, those used in the UVA range (320–400 nm) are afflicted with problems, because compounds of this type, such as, for example, the dibenzoylmethanes Parsol® 1789 or Eusolex® 8020 are not unlimitedly stable under UV irradiation, which on the one hand reduces the effectiveness of the filter with time and on the other hand can favour photosensitization of the skin. The benzophenones also used as UVA filters are only limitedly soluble in the oils used in the field of cosmetics and have a relatively low absorption. However, only a few water-soluble UVA filters are currently known, the UV absorption of which, however, is low.

Benzylidenecamphor derivatives are known from German Offenlegungsschrift 3,833,706, corresponding to U.S. Pat. No. 5,000,961. However, these have at least one tertiary alkyl group. Compounds of this type can admittedly also be used as UV filters in sunscreens, but are suitable rather as antioxidants on account of the phenolic hydroxyl group. On account of their tertiary alkyl group, these compounds are only limitedly soluble in conventional cosmetic excipients, in particular in aqueous suspensions, so that they always have to be employed in sunscreens together with other UV filters.

An object of the invention is novel compounds which can be used for the preparation of cosmetic and/or pharmaceutical preparations and do not have the above-mentioned disadvantages.

It has been found that the compounds of the formula I and their physiologically acceptable acid addition salts have useful cosmetic and pharmaceutical properties. The compounds of the formula I are thus substances having outstanding UVA filter properties. Their solubility in the oils used in the field of cosmetics is very good, so that use concentrations up to at least 10% of the preparation are possible even in complicated formulations.

Compounds of the formula I having relatively long-chain alkoxy groups, such as, for example, the 2-ethylhexyloxy group, are in some cases miscible in any ratio with conventional cosmetic solvents, such as Miglyol or paraffin.

The absorption of the compounds moreover exhibits a minimum in the UVB range; however, this is not a disadvantage, since a UVB filter can additionally be incorporated into the formulation without problems.

In addition, the compounds of the formula I can also be used for the prophylactic treatment of inflammations and allergies of the skin and for the prevention of certain types of cancer.

Apart from their good properties as filters, the compounds according to the invention are distinguished by a good thermal and photochemical stability.

These compounds also offer the advantage of not being toxic or irritant and being completely harmless to the skin.

They disperse uniformly in the conventional cosmetic excipients and can form a continuous film, in particular in excipients based on fats; in this way, they can be applied to the skin to form an effective protective film.

The invention relates to compounds of the above-mentioned formula. I.

In this formula, $R^1$ is A. A is a straight-chain or branched alkyl radical having 1–10 C atoms. In particular, A is methyl, ethyl, propyl, isopropyl, butyl, isobutyl, sec-butyl, tert-butyl, pentyl, hexyl, 2-,3-,4- or 5-methylhexyl, 2-,3-,4- or 5-ethylhexyl, or heptyl.

$R^2$, $R^3$, $R^4$ and $R^5$ in each case independently of one another are a hydrogen atom, A, OH or OA, where A preferably corresponds to one of the preferred alkyl radicals mentioned previously.

The invention accordingly relates in particular to those compounds of the formula I in which at least one of the said radicals has one of the abovementioned meanings, in particular the abovementioned preferred meanings. Some preferred groups of compounds can be expressed by the following sub-formulae Ia to If, which correspond to the formula I and in which the radicals and parameters which are not described in greater detail have the meaning given under formula I, but in which in Ia $R^1$ is 2-ethylhexyl;
in Ib $R^1$ is 2-ethylhexyl and one of the radicals $R^2$, $R^3$, $R^4$ or $R^5$ is methoxy;
in Ic $R^1$ is methyl and one of the radicals $R^2$, $R^3$, $R^4$ or $R^5$ is 2-ethylhexyloxy;
in Id $R^1$ is methyl;
in Ie $R^1$ is methyl and one of the radicals $R^2$, $R^3$, $R^4$ or $R^5$ is methoxy;
in If $R^1$ is methyl and two of the radicals $R^2$, $R^3$, $R^4$ and/or $R^5$ are methoxy.

The particularly preferred compounds of the formula I include:
2-(4-(2-ethylhexyloxy)benzylidene)quinuclidin-3-one;
2-(4-(2-ethylhexyloxy)-3-methoxybenzylidene)quinuclidin-3-one;
2-(3-(2-ethylhexyloxy)-4-methoxybenzylidene)quinuclidin-3-one;
2-(4-methoxybenzylidene)quinuclidin-3-one;
2-(3,4-dimethoxybenzylidene)quinuclidin-3-one;
2-(2,4,5-trimethoxybenzylidene)quinuclidin-3-one.

The invention also relates to a process for the preparation of benzylidenequinuclidinone compounds of the formula I and of their salts, characterized in that 3-quinuclidinone is reacted with a compound of the formula II

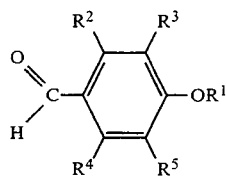

in which the radicals $R^1$, $R^2$, $R^3$, $R^4$ and $R^5$ have the given meanings,
or in that a compound otherwise corresponding to the formula I, but which instead of one or more hydrogen atoms contains one or more solvolysable groups, is treated with a solvolysing agent,
or in that a compound which otherwise corresponds to the formula I, but instead of one or more H atoms contains a cleavable protective group, is converted into a compound of the formula I by cleavage of this protective group,
or in that in a compound of the formula I according to claim 1 one or more of the radicals $R^2$, $R^3$, $R^4$ and/or $R^5$ are converted into one or more other radicals $R^2$, $R^3$, $R^4$ and/or $R^5$
and/or in that a base of the formula I obtained is converted into one of its salts by treatment with an acid.

The compounds of the formula I are otherwise prepared by methods known per se, such as are described in the literature (for example in standard works such as Houben-Weyl, Methoden der Organischen Chemie [Methods of Organic Chemistry], Georg Thieme Verlag, Stuttgart; Organic Reactions, John Wiley & Sons, Inc., New York), namely under reaction conditions such as are known and suitable for the said reactions.

Use can also be made in this case of variants known per se and not mentioned in greater detail here.

If desired, the starting substances for the claimed process can also be formed in situ in such a way that they are not isolated from the reaction mixture, but immediately reacted further to give the compounds of the formula I.

In the compounds of the formula II, $R^1$ is preferably ethyl, propyl, isopropyl, butyl, tert-butyl, sec-butyl, isobutyl or particularly preferably methyl or 2-ethylhexyl.

The radicals $R^2$, $R^3$, $R^4$ and $R^5$ are preferably H or OA, such as, for example, methoxy, ethoxy, propoxy or else alternatively 2-ethylhexyloxy. In particularly preferred compounds of the formula II one or two of the radicals $R^2$, $R^3$, $R^4$ and/or $R^5$ are OA, while the rest correspond to hydrogen atoms.

The compounds of the formula II are mainly known; the unknown compounds of the formula II can easily be prepared in analogy to the known compounds.

The aldehydes of the formula II can be prepared, for example, by oxidation of the corresponding alcohols or by reduction of the corresponding carboxylic acids by methods known per se. Further suitable processes for the synthesis of the aromatic aldehydes of the formula II are, for example, the Reimer-Tiemann, Vilsmeier-Haack or Gartermann-Koch synthesis, but other processes not mentioned here in greater detail can also be used for the preparation.

The reaction of the compounds of formula II with 3-quinuclidinone proceeds according to methods such as are known from the literature for the condensation of aldehydes and ketches (cf. for this Houben-Weyl, Methoden der Organ. Chemic [Methods of Organic Chemistry] Vol. 7/26, Georg-Thieme-Verlag Stuttgart (1976); Modern Synthetic React. 2nd ed., 629–682 (1972)).

For example, the components can be fused with one another without the presence of a solvent, if appropriate in a closed tube or in an autoclave. However, it is also possible to react the compounds in the presence of an indifferent solvent. Suitable solvents are, for example, hydrocarbons such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, and if appropriate also mixtures of these solvents with one another or mixtures with water. The addition of an acid-binding agent, for example, an alkali metal or alkaline earth metal hydroxide, a carbonate or bicarbonate, or another salt of a weak acid of the alkali metals or alkaline earth metals, preferably potassium, sodium or calcium, or the addition of an organic base such as triethylamine, dimethylaniline, pyridine or quinoline may be favorable. Depending on the conditions used, the reaction time is between a few minutes and 14 days, and the reaction temperature between about 0° and 150°, normally between 20° and 130°.

Compounds which otherwise correspond to the formula I, but instead of one or more H atoms contain one or more solvolysable groups, can also be solvolysed, in particular hydrolysed, to give compounds of the formula I.

The starting substances for the solvolysis are, for example, obtainable by reaction of compounds which correspond to the formula II, but instead of one or more H atoms contain one or more solvolysable groups, with 3-quinuclidinone. Compounds of the formula I which carry an acyloxy group on the aromatic ring, preferably an alkanoyl, alkylsulfonyl or arylsulfonyl group in each case having up to 10 C atoms, such as, for example, methane-, benzene- or p-toluenesulfonyl, can thus in particular be hydrolysed to the corresponding unsubstituted hydroxy derivatives, for example in acidic medium, better in neutral or alkaline medium, at temperatures between 0° and 200°. Bases used are expediently sodium hydroxide, potassium hydroxide or calcium hydroxide, sodium carbonate or potassium carbonate, or ammonia. Solvents selected are preferably water; lower alcohols such as methanol, ethanol; ethers such as THF, dioxane; sulfones such as tetramethylene sulfone; or mixtures thereof, particularly the water-containing mixtures. Hydrolysis can also be carried out during treatment with water on its own, in particular at boiling heat.

Compounds of the formula I which contain an O-alkyl group can be converted into the corresponding hydroxy derivatives by ether cleavage. For example, the ethers can be cleaved by treatment with dimethyl sulfide-boron tribromide complex, for example in toluene, ethers such as THF or dimethyl sulfoxide, or by fusion with pyridine or aniline hydrohalides, preferably pyridine hydrochloride, at about 150°–250°.

Under certain circumstances, the compounds of the formula I may possess one or more centers of asymmetry if one of the radicals $R^1-R^5$ is chiral. They can therefore be obtained in their preparation as racemates or, if optically active starting substances are used, also in optically active form. If the compounds contain two or more centers of asymmetry, then they are in general obtained in the synthesis as mixtures of racemates from which the individual racemates can be isolated in pure form, for example by recrystallization from inert solvents. Racemates obtained can be separated, if desired, into their optical antipodes mechanically or chemically by methods known per se. Preferably, diastereomers are formed from the racemate by reaction with an optically active resolving agent. Suitable resolving agents are, for example, optically active acids, such as the D- and L-forms of tartaric acid, dibenzoyltartaric acid, diacetyltartaric acid, camphorsulfonic acids, mandelic acid, malic acid or lactic acid. The various forms of the diastereomers can be separated in a manner known per se, for example by fractional crystallization, and the optically active compounds of the formula I can be set free from the diastereomers in a manner known per se.

A base of the formula I obtained can be converted into the associated acid addition salt using an acid. Acids which give physiologically acceptable salts are suitable for this reaction. Inorganic acids can thus be used, for example sulfuric acid, hydrohalic acids such as hydrochloric acid or hydrobromic acid, phosphoric acids such as orthophosphoric acid, nitric acid, sulfamic acid, also organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene mono- and -disulfonic acids, and laurylsulfuric acid.

In all cases where the compounds of the formula I have acidic phenolic OH groups, salt formation can be achieved by treatment with bases. Suitable bases are alkali metal hydroxides, alkaline earth metal hydroxides or organic bases in the form of primary, secondary or tertiary amines.

The invention also relates to the use of the compounds of the formula I and their physiologically acceptable salts for the production of pharmaceutical preparations, in particular by non-chemical routes. In this process, they can be brought into a suitable dose form together with at least one excipient or auxiliary and if appropriate in combination with one or more further active substances.

The invention also relates to compositions, in particular pharmaceutical preparations, containing at least one compound of the formula I and/or one of its physiologically acceptable salts. These preparations can be employed as medicaments in human and veterinary medicine. Suitable excipients are organic or inorganic substances which are suitable for parenteral or topical application and which do not react with the novel compounds, for example water, vegetable oils, benzyl alcohols, polyethylene glycols, gelatine, talc or petroleum jelly. Solutions, preferably oily or aqueous solutions, also suspensions, emulsions or implants are suitable for parenteral administration, and ointments, creams, gels, sticks or powders for topical application.

The given preparations can be sterilized and/or contain auxiliaries such as lubricants, preservatives, stabilizers and/or wetting agents, emulsifiers, salts for affecting the osmotic pressure, buffer substances, colorants and/or aromatizers. If desired, they can also contain one or more further active substances, for example one or more vitamins.

The compounds of the formula I and their physiologically acceptable salts can be used in therapeutic treatment and for the prevention of dermatological disorders of the human or animal body. They are suitable for the treatment of numerous disorders of the skin, in particular those which have been produced by intensive solar irradiation. The compounds of the formula I exhibit a significant pharmacological activity in the field of the preventive treatment of inflammations and/or skin allergies.

The substances according to the invention are as a rule administered here parenterally, in analogy to known, commercially available preparations, preferably in doses between about 0.1 and 400 mg, in particular between 0.2 and 50 mg per dose unit. The specific dose for each individual patient depends, however, on the most diverse factors, for example on the activity of the specific compound employed, on the age, body weight, general state of health, sex, on the diet, on the administration time and route, medicament combination and severity of the respective disorder to which the therapy applies. Topical application is preferred.

The invention further relates to the use of the novel compounds of the formula I for the production of cosmetic preparations which contain an effective amount of at least one benzylidenequinuclidinone compound of the formula I in cosmetically tolerable excipients.

Those cosmetic preparations are particularly preferred in which the excipient contains at least one fatty phase, or those in which the excipient contains at least one aqueous phase.

The cosmetic composition according to the invention can be used as a composition for the protection of the human epidermis and/or of the hair or as a sunscreen.

If the cosmetic composition according to the invention is used as a composition for the protection of the human epidermis against UV rays, it is present in various forms customarily used for this type. It can thus be present in particular in the form of oily or oily-alcoholic lotions, emulsions, such as a cream or as a milk, in the form of oily-alcoholic, oily-aqueous or aqueous-alcoholic gels or as solid sticks, or formulated as an aerosol.

It can contain cosmetic adjuvants which are customarily used in this type of composition, such as, for example, thickeners, softening agents, moisturizers, surface-active agents, preservatives, foam preventatives, perfumes, waxes, lanolin, propellants, colorants and/or pigments which color the composition itself or the skin, and other ingredients usually used in cosmetics.

The compound of the formula I may be present in an amount, generally form 1 to 10%, relative to the total weight of the cosmetic composition for the protection of the human epidermis. The amount of the compound incorporated into the composition is determined conventionally.

As a solubilizer, an oil, wax or other fatty compound, a lower monoalcohol or a lower polyol or mixtures thereof can be Used. The particularly preferred monoalcohols or polyols include ethanol, i-propanol, propylene glycol, glycerol and sorbitol.

A preferred embodiment of the invention is an emulsion which is present as a protective cream or milk and apart from the compound of the formula I includes fatty alcohols, fatty acid esters, in particular triglycerides of fatty acids, fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The cosmetic composition according to the invention can also be present as an alcoholic gel which includes one or more lower alcohols or polyols, such as ethanol, propylene glycol or glycerol, and a thickener, such as silica. The oily-alcoholic gels additionally contain natural or synthetic oil or wax.

The solid sticks contain natural or synthetic waxes and oils, fatty alcohols, fatty acid esters, lanolin and other fatty compounds.

The invention also relates to cosmetic sunscreens which contain at least one compound of the formula I and include other UVB and/or UVA filters.

In the latter case, the amount of the filter of the compound of formula I is generally between 1.0 and 8.0% by weight, relative to the total weight of the sunscreen.

If a composition is formulated as an aerosol, generally the customary propellants, such as alkanes, fluoroalkanes and chlorofluoroalkanes, are used.

If the composition according to the invention is intended to protect natural or sensitized hair from UV rays, it can be present as a shampoo, lotion, gel or emulsion for rinsing out, the respective formulation being applied before or after shampooing, before or after dyeing or bleaching, or before or after the perm; or the composition is present as a lotion or gel for hair-styling and treating, as a lotion or gel for brushing or setting a water-wave, or as a hair lacquer, permanent waving agent, or hair-dying or -bleaching agent. Apart from the compound according to the invention, this composition can contain various adjuvants used in this type of composition, such as surface-active agents, thickeners, polymers, softening agents, preservatives, foam stabilizers, electrolytes, organic solvents, silicone derivatives, oils, waxes, degreasing agents, dyes and/or pigments which dye the composition itself or the hair or other ingredients customarily used for hair care. The composition as a rule contains 1.0 to 5.0% by weight of the compound of the formula I.

The present invention is also concerned with cosmetic compositions which contain at least one compound of the formula I as agents for protection from UV rays and as antioxidants; these compositions include make-up products, such as nail varnish, creams and oils for skin treatment, make-up (foundation cream), lipsticks, skin care compositions, such as bath oils or creams and other cosmetic compositions which can raise problems with light stability and/or oxidation in the course of storage with respect to their components. Compositions of this type generally contain 1.0. to 5.0% by weight of a compound of the formula I.

The invention is also concerned with a process for the protection of the cosmetic compositions from UV rays and oxidation, an effective amount of at least one compound of the formula I being added to these compositions.

The invention further relates to the use of the compounds of the formula I as sun filters of wide absorption in a wavelength range from 320 to 400 nm.

The invention further relates to the use of the compounds of the formula I in combination with suitable UV-B filters as cosmetic products.

The UV-B filters used can be commercially available products, such as, for example, Eusolex ® 6300 or Eusolex ® 232.

Upon further study of the specification and appended claims, further objects and advantages of this invention will become apparent to those skilled in the art.

The entire disclosure of all applications, patents and publications, cited above and below, and of corresponding German application No. P 42 21 740.7, filed Jul. 2, 1992, are hereby incorporated by reference.

In the Examples below, "customary working up" means: if necessary, water is added, the mixture is extracted with dichloromethane, the organic phase is separated off, dried over sodium sulfate or magnesium sulfate, filtered and evaporated and the residue is purified by chromatography on silica gel and/or by crystallization. The UV measurements were carried out by conventional methods, 1 mg of the respective substance being dissolved in 100 ml of ethanol (c=1 mg/100 ml). The respective extinction (E) was determined arithmetically from the value $\lambda_{max}$ determined by measurement.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

EXAMPLES

A and B refer to the solutions used to provide the ingredients present in the two phases of the emulsions.

Example 1

A solution of 16.0 g of 3-quinuclidinone (hydrochloride) in 100 ml of water is treated with 100 ml of a 32% sodium hydroxide solution. 36.0 g of 4-(2-ethylhexyloxy)benzaldehyde [can be prepared from p-hydroxybenzaldehyde by reaction with 1-chloro-2-ethylhexane], dissolved in 250 ml of ethanol, is then added with stirring and the mixture is heated under reflux for 3 hours. After the reaction is complete, it is worked up in the customary manner. 2-[4-(2-ethylhexyloxy)benzylidene]-quinuclidin-3-one is obtained in the form of a pale yellow solid; m.p. 37°, $\lambda_{max}=331$ nm, E=0.8.

The following are obtained analogously by reaction of 3-quinuclidinone (hydrochloride)

with 4-(2-ethylhexyloxy) -3-methoxybenzaldehyde 2-[4-(2-ethylhexyloxy)-3-methoxybenzylidene]-quinuclidin-3-one, m.p. 58°, $\lambda_{max}=342$ nm, E=0.6;

with 3-(2-ethylhexyloxy) -4-methoxybenzaldehyde 2-[3-(2-ethylhexyloxy)-4-methoxybenzylidene]-quinuclidin-3-one, oily, $\lambda_{max}=341$ nm, E=0.56;

with 4-methoxybenzaldehyde 2-(4-methoxybenzylidene)quinuclidin-3-one, m.p. 123°, $\lambda_{max}=327$ nm, E=1.1;

with 3,4-dimethoxybenzaldehyde 2-(3,4-dimethoxybenzylidene)quinuclidin-3-one, m.p. 103°, $\lambda_{max}=338$ nm, E=0.8;

with 2,4,5-trimethoxybenzaldehyde 2-(2,4,5-trimethoxybenzylidene)quinuclidin-3-one, m.p. 119°, $\lambda_{max}=370$ nm, E=0.6.

Example 2

The following are obtained analogously to Example 1 by reaction of 3-quinuclidinone with 4-(2-ethylpentyloxy)-2-methoxybenzaldehyde 2-[4-(2-ethylpentyloxy)-2-methoxybenzylidene]-quinuclidin-3-one with 4-(2-methylpropyloxy)-3-methoxybenzaldehyde 2-[4-(2-methylpropyloxy)-3-methoxybenzylidene]-quinuclidin-3-one, with 3-ethoxy-4-methoxybenzaldehyde 2-(3-ethoxy-4-methoxybenzylidene)quinuclidin-3-one, with 4-propoxybenzaldehyde 2-(4-propoxybenzylidene)quinuclidin-3-one, with 2,4-dimethoxybenzaldehyde 2-(2,4-dimethoxybenzylidene)quinuclidin-3-one, with 2,4,6-trimethoxybenzaldehyde 2-(2,4,6-trimethoxybenzylidene)quinuclidin-3-one, with 4-(2-ethylhexyloxy)-3-methylbenzaldehyde 2-[4-(2-ethylhexyloxy)-3-methylbenzylidene]-quinuclidin-3-one, with 4-(2-ethylhexyloxy)-3-hydroxybenzaldehyde 2-[4-(2-ethylhexyloxy)-3-hydroxybenzylidene)-quinuclidin-3-one, with 4-ethoxybenzaldehyde 2-(4-ethoxybenzylidene)-quinuclidin-3-one, with 3,4-diethoxybenzaldehyde 2-(3,4-diethoxybenzylidene)quinuclidin-3-one, with 2,6-dimethyl-4-methoxybenzaldehyde 2-(2,6-dimethyl-4-methoxybenzylidene)quinuclidin-3-one, with 4-tert-butyloxybenzaldehyde 2-(4-tert-butyloxybenzylidene)quinuclidin-3-one, with 3-(2-methylbutyloxy)-4-methoxybenzaldehyde 2-[3-(2-methylbutyloxy)-4-methoxybenzylidene]-quinuclidin-3-one, with 2-methyl-4-methoxybenzaldehyde 2-(2-methyl-4-methoxybenzylidene)quinuclidin-3-one, with 2,5-dihydroxy-4-methoxybenzaldehyde 2-(2,5-dihydroxy-4-methoxybenzylidene)quinuclidin-3-one, with 2,6-dihydroxy-4-methoxybenzaldehyde 2-(2,6-dihydroxy-4-methoxybenzylidene)quinuclidin-3-one, with 2,6-diethyl-4-methoxybenzaldehyde 2-(2,6-diethyl-4-methoxybenzylidene)quinuclidin-3-one, with 2,6-di-tert-butyl-4-methoxybenzaldehyde 2-(2,6-di-tert-butyl-4-methoxybenzylidene)quinuclidin-3-one, with 2,6-diisopropyl-4-methoxybenzaldehyde 2-(2,6-diisopropyl-4-methoxybenzylidene)quinuclidin-3-one, with 3,5-dihydroxy-4-methoxybenzaldehyde 2-(3,5-dihydroxy-4-methoxybenzylidene)quinuclidin-3-one, with 3,5-dimethyl-4-methoxybenzaldehyde 2-(3,5-dimethyl-4-methoxybenzylidene)quinuclidin-3-one, with 3,5-diisopropyl-4-methoxybenzaldehyde 2-(3,5-diisopropyl-4-methoxybenzylidene)quinuclidin-3-one.

In the following Use Examples A to D, G and H, the following UV filters can be employed alternatively in each case:

1. 10% of compound from Example 1
2. 5% of compound from Example 1 2% of benzophenone-3 3% of octyldimethyl p-aminobenzoate (octyldimethyl paba)
3. 6% of compound from Example 1 3% of 3-(4-methylbenzylidene)camphor
4. 4% of compound from Example 1 1% of octyltriazone
5. 8% of compound from Example 1 6% of octyl methoxycinnamate
6. 6% of compound from Example 1 4% of octyl salicylate 2% of 4-isopropyldibenzoylmethane
7. 8% of compound from Example 1 2% of benzophenone-3

The company names given below in brackets give the supply source of the respective ingredients.

Use Examples

Example A: Sunscreen (O/W)

The following ingredients are mixed, optionally being heated to 70°–85° C. for homogenization; the perfume oil is added at 35°–45° C.

| | % by weight |
|---|---|
| UV filter | q.s. |
| Arlacel 165 ® "glycerol monostearate and POE stearate" (ICI, Essen) | 9.5 |
| Atlas G-1790 ® "polyoxyethylene(20) lanolin derivative" (ICI, Essen) | 6.60 |
| Lanette O ®, "cetyl stearyl alcohol", (Henkel AG) | 3.00 |
| Paraffin, highly liquid (E. Merck) | 3.00 |
| Isopropyl myristate | 1.50 |
| Abil AV 20 ® | 1.00 |
| Antioxidant containing butylhydroxytoluene "Oxynex 2004 ®" (E. Merck) | 0.02 |
| Allantoin (E. Merck) | 0.30 |
| Sorbitol "Karion ® F liquid" (E. Merck) | 6.00 |

-continued

|  | % by weight |
|---|---|
| Disodium salt of ethylenediaminetetra-acetic acid "Titriplex ®" (E. Merck) | 0.05 |
| Pantothenyl alcohol | 0.30 |
| Preservative (E. Merck) | 0.5 |
| Demineralized water | to 100 |

Example B: Sunscreen milk (O/W)

|  | % by weight |
|---|---|
| UV filter | q.s. |
| Mixture of cetyldimethicone copolyol, polyglyceryl-4-isostearate and hexyl laurate "Abil WE 09 ®" (Th. Goldschmidt) | 5.00 |
| Paraffin, highly liquid (E. Merck) | 16.00 |
| Sodium chloride (E. Merck) | 2.00 |
| Glycerol (E. Merck) | 3.00 |
| Preservative (E. Merck) | q.s. |
| Water, demineralizbd | to 100.00 |
| Perfume oil Delaila ® (Dragoco) | 0.50 |

The ingredients are mixed, optionally being heated to 70°–85° C. for homogenization; the perfume oil is added at 35°–45° C.

Example C: Sunscreen cream (W/O)

|  |  | % by weight |
|---|---|---|
| A | UV filter | q.s. |
|  | POE glycerol sorbitan oleostearate "Arlacel 581 ®" (ICI) | 7.0 |
|  | Paraffin, highly liquid (E. Merck) | 6.0 |
|  | PPG-15 stearyl ether and cyclomethicone 10 "Arlamol S 7 ®" (ICI) | 2.0 |
|  | 020 Kevit wax "Lunacera M ®" (LW Fuller) | 5.0 |
|  | Cyclomethicone "Dow Corning 344 ®" (Dow Corning) | 4.00 |
|  | Triglyceride oil "Miglyol 812 ®" (Hüls Troisdorf AG) | 2.00 |
| B | Glycerol (Item No. 4093) (E. Merck) | 2.00 |
|  | Magnesium sulfate heptahydrate (E. Merck) | 0.17 |
|  | Preservative (E. Merck) | q.s. |
|  | Water, demineralized | to 100.00 |

The ingredients are homogenized at 70°–85° C.; the preparation is optionally perfumed at 35°–45° C.

Example D: Sunscreen cream (O/W)

|  |  | % by weight |
|---|---|---|
| A | UV filter | q.s. |
|  | Mixture of cetearyl alcohol and ceteareth-20 "Emulgade 1000 Ni ®" (Henkel) | 10.00 |
|  | Paraffin, viscous (E. Merck) | 2.00 |
|  | Dimethylsiloxane "Dow Corning 200 (100 cs) ®" | 0.50 |
|  | Oxynex 2004 (E. Merck) | 0.10 |
| B | Glycerol (E. Merck) | 5.00 |
|  | Titriplex III ® (E. Merck) | 0.10 |
|  | Preservative (E. Merck) | q.s. |
|  | Water, demineralised | to 100.00 |

The ingredients are homogenized at 70° to 85° C. The preparation is optionally perfumed at 35° to 45° C.

Example E: Sunscreen cream (O/W)

|  | % by weight |
|---|---|
| Compound from Example 1 | 5.00 |
| Stearic acid (E. Merck) | 20.00 |
| Triglyceride oil "Miglyol 812 ®" (Hüls Troisdorf AG) | 20.00 |
| UV filter 2-phenylbenzimidazole-5-sulfonic acid "Eusolex 232 ®" (E. Merck) | 1.50 |
| Tris(hydroxymethyl)aminomethane (E. Merck) | 0.66 |
| Sorbitol "Karion F liquid ®" (E. Merck) | 5.00 |
| Allantoin (E. Merck) | 0.20 |
| Triethanolamine (E. Merck) | 6.00 |
| Preservative (E. Merck) | q.s. |
| Water, demineralized | to 100.00 |

To neutralize Eusolex ® 232, the tris(hydroxymethyl)aminomethane is dissolved in water and Eusolex ® 232 is added with stirring. After dissolution is complete, the residual ingredients are added at 75°–85° C. and the mixture is homogenised. Cool with stirring and optionally perfume at 40° C.

Example F:

Hairstyling gel (oil-containing) with UV filter

The compound from Example 1 can be replaced by a mixture of 2% of compound from Example 1 and 1% of benzophenone-3 or 1% of 3-(4-methylbenzylidene)camphor.

|  | % by weight |
|---|---|
| Compound from Example 1 | 3 |
| Polyoxyethylene 30 cetyl stearyl alcohol "Emulgin B 3 ®" (Henkel AG) | 13.00 |
| Polyol fatty acid ester "Cetiol HE ®" (Henkel AG) | 20.00 |
| Eutanol G ® "octyldecanol" (Henkel AG) | 5.00 |
| Preservative (E. Merck) | q.s. |
| Water, demineralized | to 100.00 |

The ingredients are mixed and homogenized at 70° to 85° C. The preparation is optionally perfumed at 35° to 45° C.

Example G: Hair treatment with UV filter (cream O/W)

|  | % by weight |
|---|---|
| UV filter | 3.00 |
| Cetyl stearyl alcohol "Lanette O ®" (Henkel AG) | 2.50 |
| Polyoxyethylene 20 stearyl alcohol "Emulgin B 2 ®" (Henkel AG) | 1.00 |
| Wax ester (jo ioba oil substitute) "Cetiol J 600 ®" (Henkel AG) | 1.00 |
| N-cetyl-N,N,N-trimethylammonium bromide (E. Merck) | 1.00 |
| Preservative (E. Merck) | q.s. |
| Water, demineralized | to 100.00 |

Preparation is carried out analogously to Example A.

Example H: Suntan oil

|  | % by weight |
|---|---|
| UV filter | q.s. |
| POE 40 sorbitol heptaoleate "Arlatone T ®" (ICI) | 2.00 |
| Triglyceride oil "Miglyol 812 ®" | 16.00 |

-continued

| | % by weight |
|---|---|
| (Hüls Troisdorf AG) | |
| Di-n-butyl adipate "Cetiol B ®" (Henkel AG) | 22.50 |
| Isopropyl myristate (Henkel AG) | 7.50 |
| Paraffin, highly liquid (E. Merck) | to 100.00 |
| Antioxidant containing butylhydroxy-toluene "Oxynex 2004 ®" (E. Merck) | 0.2 |
| Preservative | q.s. |
| Perfume oil 72979 (Haarmann & Reimer) | q.s. |

Preparation is carried out analogously to Example A.

Example I: Sunscreen gel (aqueous-alcoholic)

| | % by weight |
|---|---|
| Aqueous phase: | |
| Compound from Example 2 | 10.00 |
| Tris(hydroxymethyl)aminomethane (E. Merck) | 2.80 |
| Allantoin (E. Merck) | 0.20 |
| Sorbitol "Karion F ® liquid" (E. Merck) | 5.00 |
| Preservative | q.s. |
| Water, demineralized | to 100.00 |
| Alcoholic phase: | |
| Perfume oil (Haarmann & Reimer) | 0.30 |
| POE 35 hydrogenated castor oil "Arlatone 980 ®" (ICI) | 1.00 |
| Carboxyvinyl polymer "Carbopol 940 ®" (Goodrich) | 1.50 |
| Water, demineralized | 35.50 |
| Triethanolamine (E. Merck) | 3.00 |
| Ethanol (96%) (E. Merck) | to 100.00 |

The tris(hydroxymethyl)aminomethane is dissolved in water and the UV filter from Example 2 is added with stirring. After dissolution is complete, the remaining raw materials are added and the mixture is heated to 75° C. It is then cooled with stirring.

Example J: Sunscreen cream (O/W)

| | % |
|---|---|
| A UV filter | q.s. |
| Stearic acid (E. Merck) | 20.00 |
| Triglyceride oil "Miglyol 812" | 20.00 |
| B Compound from Example 2 (E. Merck) | 10.00 |
| Tris(hydroxymethyl)aminomethane (E. Merck) | 2.80 |
| Sorbitol "Karion F ® liquid" (E. Merck) | 5.00 |
| Allantoin (E. Merck) | 0.20 |
| Triethanolamine (E. Merck) | 6.00 |
| Preservative (E. Merck) | q.s. |
| Water, demineralized | to 100.00 |

The compounds from Example 1 or 2 can be employed alternatively as UV filters.

Preparation:

The tris(hydroxymethyl)aminomethane is dissolved in the water of Phase B and the UV filter from Example 1 is added with stirring. After dissolution is complete, the remaining raw materials of Phase B are added, and the mixture is heated to 80°. Phase A is heated to 75°. Phase B is slowly stirred into Phase A, and the mixture is homogenized, cooled with stirring and optionally perfumed at 40°.

Example K: Sunscreen cream (O/W)

| | % |
|---|---|
| A UV filter | q.s. |
| Stearic acid (E. Merck) | 20.00 |
| Triglyceride oil "Miglyol 812" (Hüls Troisdorf) | 20.00 |
| B Compound from Example 2 (E. Merck) | 5.00 |
| Sodium hydroxide (10% solution) (E. Merck) | 0.40 |
| Sorbitol "Karion F ® liquid" (E. Merck) | 5.00 |
| Allantoin (E. Merck) | 0.20 |
| Triethanolamine (E. Merck) | 6.00 |
| Preservative (E. Merck) | q.s. |
| Water, demineralized | to 100.00 |

The compounds from Example 1 or 2 can be employed alternatively as UV filters.

Preparation:

For neutralization, the UV filter is stirred into the sodium hydroxide solution and the water of Phase B. After dissolution is complete, the remaining raw materials of Phase B are added and the mixture is heated to 80°. Phase A is heated to 75°. Phase B is slowly stirred into Phase A, and the mixture is homogenised, cooled with stirring and optionally perfumed at 40°.

Example L: Sunscreen cream (O/W)

| | % |
|---|---|
| A UV filter | q.s. |
| Stearic acid (E. Merck) | 20.00 |
| Triglyceride oil "Miglyol 812" (Hüls Troisdorf) | 20.00 |
| B UV filter from Example 2 (E. Merck) | 5.00 |
| Sorbitol "Karion F ® liquid" (E. Merck) | 5.00 |
| Allantoin (E. Merck) | 0.20 |
| Triethanolamine (E. Merck) | 6.17 |
| Preservative (E. Merck) | q.s. |
| Water, demineralized | to 100.00 |

The compounds from Example 1 or 2 can be employed alternatively as UV filters.

Preparation:

The triethanolamine is dissolved in the water of Phase B and the UV filter of Example 1 is added with stirring. After dissolution is complete, the remaining raw materials of Phase B are added and the mixture is heated to 80°. Phase A is heated to 75°. Phase B is slowly stirred into Phase A, and the mixture is homogenized, cooled with stirring and optionally perfumed at 40°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A benzylidenequinuclidinone compound of the formula I

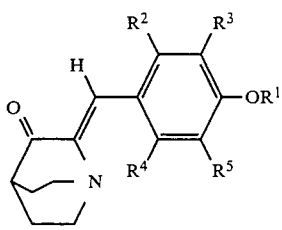

in which

R¹ is A;

R², R³, R⁴ and R⁵ are in each case independently of one another H, A, OA or OH; and A is a straight-chain or branched alkyl radical having 1 to 10 C atoms; and salts thereof, with the proviso that together R¹ is not methyl and R³ and R⁵ are not methoxy; and benzylidene is not monomethoxy, dimethoxy, or monoethoxy.

2. A compound according to claim 1, which is
2-(4-(2-ethylhexyloxy)benzylidene)quinuclidin-3-one;
2-(4-(2-ethylhexyloxy)-3-methoxybenzylidene)quinuclidin-3-one;
2-(3-(2-ethylhexyloxy)-4-methoxybenzylidene)quinuclidin-3-one;
2-(2,4,5-trimethoxybenzytidene) quinuclidin-3-one.

3. A compound according to claim 1, wherein R¹ is 2-ethylhexyl.

4. A compound according to claim 1, wherein R¹ is 2-ethylhexyl and one of the radicals R², R³, R⁴ or R⁵ is methoxy.

5. A compound according to claim 1, wherein R¹ is methyl.

6. A compound according to claim 1, wherein R¹ is methyl and one of the radicals R², R³, R⁴ or R⁵ is 2-ethylhexyloxy.

7. A compound according to claim 1, wherein R¹ is methyl and one of the radicals R², or R⁴ is methoxy.

8. A compound according to claim 1, wherein A is methyl, ethyl, propyl, isopropyl, butyl, isobutyl, sec-butyl, tert-butyl, pentyl, hexyl, 2-, 3-, 4- or 5-methylhexyl, 2-, 3-, 4- or 5-ethylhexyl, or heptyl.

9. A compound according to claim 1, wherein R², R³, R⁴ and R⁵ are in each case independently of one another H, methoxy, ethoxy, propoxy, or 2-ethylhexyloxy.

10. A pharmaceutical preparation comprising a compound of the formula I, according to claim 1, and/or one of its physiologically acceptable salts and a physiologically acceptable carrier.

11. In a method of protecting human epidermis or hair against UV rays, the improvement comprising administering an effective amount of a compound of formula I

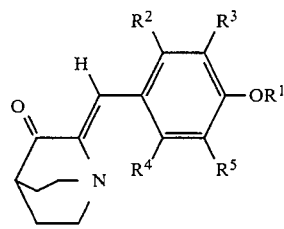

in which

R¹ is A;

R², R³, R⁴ and R⁵ are in each case independently of one another H, A, OA or OH; and A is a straight-chain or branched alkyl radical having 1 to 10 C atoms; and salts thereof.

12. A method for the treatment of inflammation and/or allergies of the skin, comprising administering an effective amount of a compound of formula I

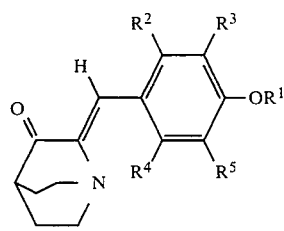

in which

R¹ is A;

R², R³, R⁴ and R⁵ are in each case independently of one another H, A, OA or OH; and A is a straight-chain or branched alkyl radical having 1 to 10 C atoms; and salts thereof.

13. A method according to claim 12, wherein the compound is administered topically.

* * * * *